(12) United States Patent
Ford et al.

(10) Patent No.: US 8,201,854 B2
(45) Date of Patent: Jun. 19, 2012

(54) HYBRID FERRULE

(75) Inventors: Douglas W. Ford, West Linn, OR (US); Robert DeLine, Cobett, OR (US)

(73) Assignee: Optimize Technologies, Inc., Oregon City, OR (US)

( * ) Notice: Subject to any disclaimer, the term of this patent is extended or adjusted under 35 U.S.C. 154(b) by 433 days.

(21) Appl. No.: 12/476,931

(22) Filed: Jun. 2, 2009

(65) Prior Publication Data
US 2009/0295156 A1 Dec. 3, 2009

Related U.S. Application Data

(60) Provisional application No. 61/058,091, filed on Jun. 2, 2008.

(51) Int. Cl.
*F16L 25/00* (2006.01)
(52) U.S. Cl. .................. 285/385; 285/384
(58) Field of Classification Search .......... 277/616; 285/384, 3, 353, 921, 385
See application file for complete search history.

(56) References Cited

U.S. PATENT DOCUMENTS

| | | | | |
|---|---|---|---|---|
| 2,663,753 A * | 12/1953 | Bird | | 174/88 C |
| 3,332,708 A * | 7/1967 | Jackson et al. | | 285/3 |
| 3,893,716 A * | 7/1975 | Moreiras et al. | | 285/3 |
| 4,205,417 A * | 6/1980 | Mackal | | 24/537 |
| 5,375,887 A * | 12/1994 | Johnson | | 285/12 |
| 5,472,598 A * | 12/1995 | Schick | | 210/198.2 |
| 5,669,637 A * | 9/1997 | Chitty et al. | | 285/342 |
| 6,095,572 A | 8/2000 | Ford | | |
| 6,494,500 B1 * | 12/2002 | Todosiev et al. | | 285/342 |
| 7,014,222 B1 * | 3/2006 | Poppe | | 285/332.1 |
| 7,316,777 B2 * | 1/2008 | Loy, Jr. | | 210/198.2 |
| 2010/0148501 A1 * | 6/2010 | Bennett et al. | | 285/382.7 |
| 2010/0224543 A1 * | 9/2010 | Ellis et al. | | 210/198.2 |
| 2010/0224546 A1 * | 9/2010 | Ellis et al. | | 210/232 |
| 2011/0107823 A1 * | 5/2011 | Dehmer | | 73/64.56 |

OTHER PUBLICATIONS

Batts, IV, J. W., "all about Fittings." www.upchurch.com Internet Archive <http://web.archive.org/web/20061111132212/www.upchurch.com/PDF/Lit/fittingsbook.pdf>, May 29, 2007.
Sonnenschein, A. and Knauer, H., "Dynaseal-Connection System for HPLC", Chromatographia vol. 22(7-12), Dec. 1986.
Valco Fittings. www.vici.com. Internet Archive <http://web.archive.org/web/20061016005832/www.vici.com/vfit/ferrules.php>, May 20, 2007.

* cited by examiner

*Primary Examiner* — Aaron Dunwoody
(74) *Attorney, Agent, or Firm* — Christensen O'Connor Johnson Kindness PLLC

(57) ABSTRACT

A ferrule for use in a fluid transfer assembly having a fluid conduit includes a frusto-conical seal portion having a first cylindrical bore sized and configured to slidably receive a fluid conduit. The seal portion is formed from a first material suitable to seal the fluid conduit within a first fitting without substantially deforming the fluid conduit. A frusto-conical collet portion is mated with the seal portion and includes a second cylindrical bore in substantial alignment with the first cylindrical bore. The collet portion includes at least one axial finger extending along the tapered end that is configured to be biased into locking engagement with the fluid conduit. The collet portion is formed from a second material that substantially prevents deformation of the fluid conduit when the finger is biased into locking engagement with the fluid conduit.

21 Claims, 5 Drawing Sheets

HYBRID FERRULE

CROSS-REFERENCE TO RELATED APPLICATION

This application claims the benefit of U.S. Provisional Application No. 61/058,091, filed Jun. 2, 2008, the disclosure of which is hereby expressly incorporated by reference.

BACKGROUND

Numerous types of equipment used for the analysis or purification of chemical compounds utilize miniature fluid conduits, such as metallic tubing, through which liquid samples pass. An analytical technique, such as liquid chromatography, uses a column (conduit) packed with a packing material in order to analyze and identify chemical properties of certain fluids. For example, an analyte may be introduced into one end of the column, and a carrier fluid then run through the column. The length of time that the analyte is retained within the column can enable analysis and identification of the analyte. A popular form of liquid chromatography is High Performance Liquid Chromatography (HPLC) in which the sample is pumped through the column under an elevated pressure, typically at 300 to 6,000 psi. Another, relatively newer liquid chromatography form is Ultrahigh Pressure Liquid Chromatography (UHPLC) in which system pressure extends upward to 1400 bar or 20,000 psi, and possibly 30,000 psi. Both HPLC and UHPLC are examples of analytical instrumentation that utilize fluid transfer at elevated pressures.

Liquid chromatography systems, such as HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly absorbed chemical material; the HPLC column itself; and a detector that analyzes the carrier fluid as it leaves the column. These various components may typically be connected by a miniature fluid conduit, such as metallic or polymeric tubing, usually having an internal diameter of 0.003 to 0.040 inch.

All of these various components and lengths of tubing are typically interconnected by threaded fittings. Fittings for connecting various components and lengths of tubing are disclosed in prior patents and patent applications, for example, U.S. Pat. Nos. 5,525,303; 5,730,943; 5,911,954; and 6,095,572; and U.S. Patent Application Publication No. 2008/0237112, filed on Jan. 9, 2008, the disclosures of which are herein all incorporated by reference.

A typical threaded fitting 18 well known in the art is shown in FIG. 1. The threaded fitting 18 includes an internally threaded portion 20 formed near its open end that is suitable for threadably receiving a second fitting, tightening device, etc., having an external threaded portion (not shown). The fitting 18 further includes an internal passageway 24 that narrows in diameter at its distal terminus to form a female, cone-shaped chamber 28 defining a frusto-conical sealing surface 26. The cone-shaped chamber 28 is in communication with a cylindrical chamber 32 sized to receive tubing 34 therein. The cylindrical chamber 32 defines a "tube stop" 30 at its end that closely and fully receives the tip of the tubing 34.

Often, the tubing interfaces with the threaded fittings with a ferrule or similar sealing device (see ferrule 36 in FIG. 1). The ferrule includes a cone-shaped end that allows it to be compressed within the female cone-shaped chamber of the fitting and thus form a liquid-tight seal. As is well known in the art, the tubing must be seated on the bottom of the cylindrical chamber when the ferrule is received within the fitting in order to ensure good chromatography. This becomes even more critical in UHPLC where the negative effects are greater. If the tube is not bottomed out in the cylindrical chamber, the resulting chromatogram exhibits band broadening due to mixing of the sample with the mobile phase. The extra volume between the end of the tube and the cylindrical chamber bottom is known as "dead volume." It is preferred that all fitting connections after the pump be made as "zero-dead-volume" connections to keep band broadening to a minimum. Even in connections before the pump it can be critical that there is "zero-dead-volume" because the extra volume will change the exact nature of mixing solvents, giving a different delay volume from various fitting connections.

The ferrule also secures on the tubing to prevent the tubing from ejecting from the fitting at specified pressures. For instance, HPLC ferrules are typically rated for pressures up to 6,000 PSI, and UHPLC ferrules are typically rated for pressures up to 20,000 PSI. In UHPLC systems, stainless steel tubing is often used to accommodate the high pressures. The ferrules are also typically made of stainless steel to properly seal against the tubing and to prevent the tubing from ejecting at the high pressures. When the ferrule is forced into the female cone-shaped chamber of the fitting, the ferrule swages down onto the tubing to prevent the tubing from ejecting from the fitting. However, with the ferrule being made of stainless steel, the ferrule swages onto the stainless steel tubing as a hard swage. As such, the position of the stainless steel ferrule cannot be readjusted on the tube, if, for instance, it is desired to use the tubing with a different fitting or component. Thus, if the stainless steel ferrule/tubing is reused in a fitting of a slightly different size, a "dead volume" is likely created between the end of the tube and the cylindrical chamber tube stop, or the ferrule cannot seat in the female cone-shaped chamber of the fitting, thereby causing the connection to leak.

In HPLC systems, a ferrule made of a softer material may be used such that a hard swage does not result. For instance, a ferrule made from Polyetheretherketone (PEEK) or another similar material may be used to seal the tubing within the fitting. The PEEK ferrule creates a soft swage on the tubing; and therefore, the position of the PEEK ferrule can be adjusted for use within different fittings. However, PEEK ferrules cannot withstand the extreme pressures of UHPLC systems.

Thus, it is desired to have a ferrule that can be re-used in various UHPLC fittings while maintaining a liquid-tight seal and preventing the tubing from ejecting at high pressures.

SUMMARY

A ferrule for use in a fluid transfer assembly having a fluid conduit is provided. The ferrule includes a frusto-conical seal portion having a tapered end and an enlarged end and a first cylindrical bore sized and configured to slidably receive a fluid conduit. The seal portion is formed from a first material suitable to seal the fluid conduit within a first fitting without substantially deforming the fluid conduit.

The ferrule further includes a frusto-conical collet portion having a tapered end and an enlarged end, wherein the enlarged end of the collet portion is mated with the enlarged end of the seal portion. The collet portion has a second cylindrical bore in substantial alignment with the first cylindrical bore and at least one axial finger extending along the tapered end that is configured to be biased into locking engagement with the fluid conduit. The collet portion is formed from a second material that substantially prevents deformation of the fluid conduit when the finger is biased into locking engagement with the fluid conduit.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated by reference to the following detailed description, when taken in conjunction with the accompanying drawings, wherein.

DETAILED DESCRIPTION

Figure 2:
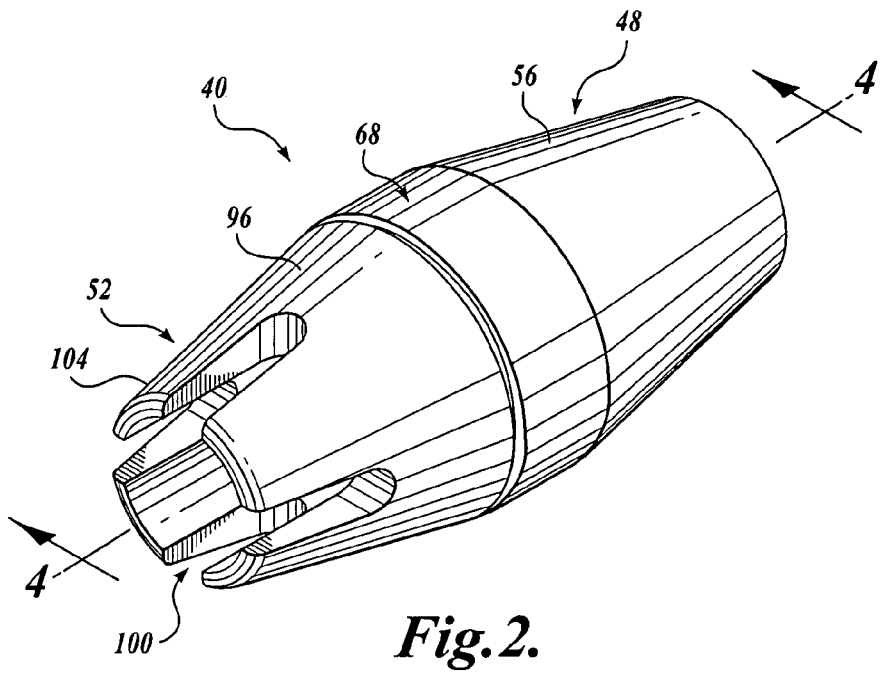
FIG. 2 is an isometric view of a hybrid ferrule formed in accordance with one embodiment of the present disclosure.
Figure 3:
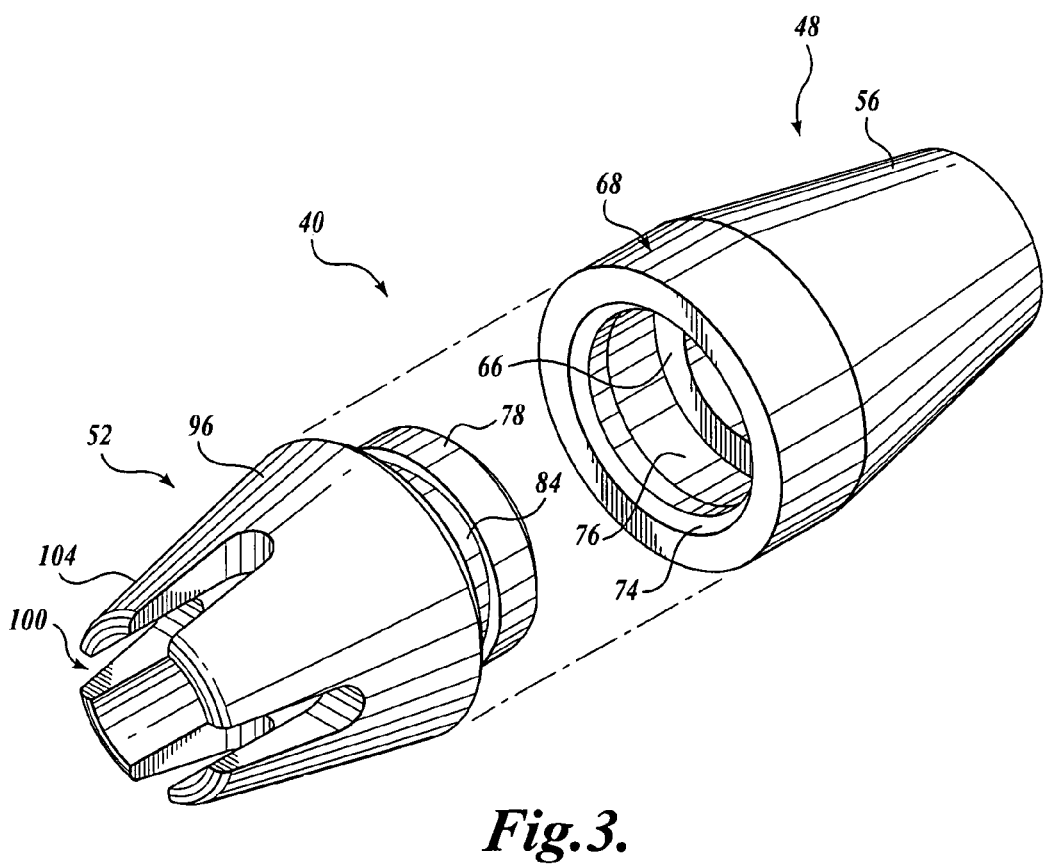
FIG. 3 is an exploded view of the hybrid ferrule of FIG. 2.
Figure 4:
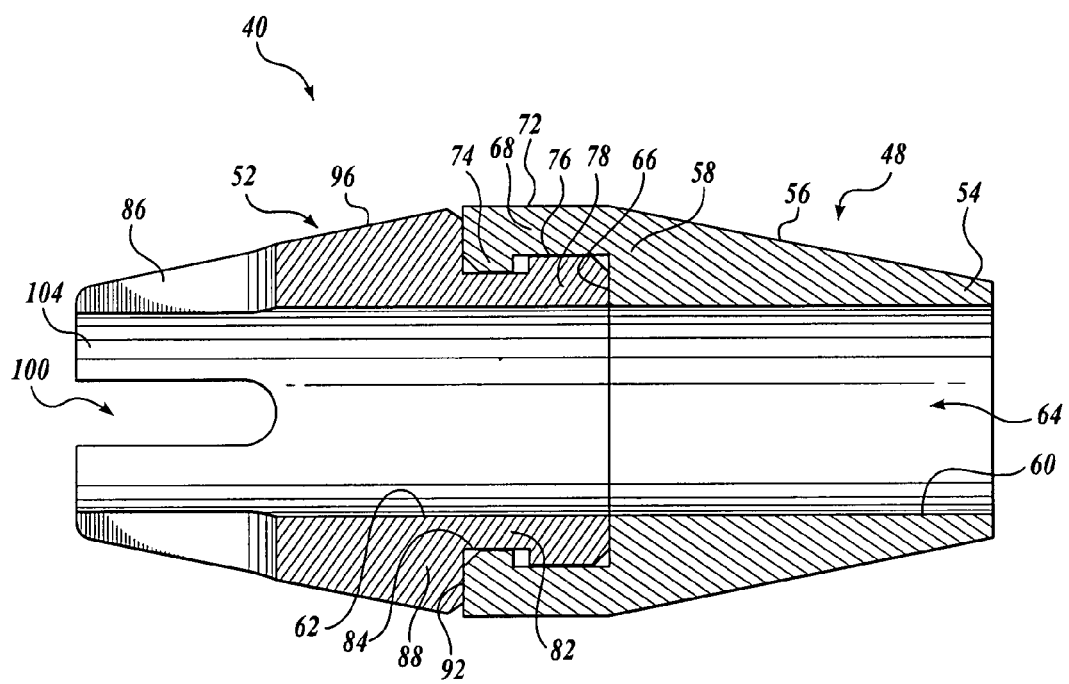
FIG. 4 is cross-sectional view of the hybrid ferrule of FIG. 2, taken substantially across line 4-4.

Referring to FIGS. 2-4, a hybrid ferrule 40 formed in accordance with one embodiment of the present disclosure is depicted. The hybrid ferrule 40 is suitable for use in fluid transfer assemblies for scientific instruments such as HPLC and UHPLC systems. For ease of description and illustration, the hybrid ferrule 40 will be hereinafter described as being used in a portion of a UHPLC fitting assembly 44. However, it should be appreciated that the hybrid ferrule 40 may instead be used in any suitable system or assembly. Thus, the description hereinafter provided should not be seen as limiting the scope of the claimed subject matter.

Referring still to FIGS. 2-4, the hybrid ferrule 40 will now be described in detail. The hybrid ferrule 40 includes a seal portion 48 mated with a collet portion 52. The seal portion 48 is formed from a material suitable for sealing within the UHPLC fitting assembly 44, such as Polyetheretherketone (PEEK), and the collet portion 52 is formed from a material suitable for gripping onto the tubing of the fitting assembly 44, such as hardened Titanium alloy. The design and materials of the hybrid ferrule 40 allow the ferrule 40 to seal within a threaded fitting and withstand the extreme pressures of UHPLC, while at the same time being adjustable and reusable within various fittings, as will become apparent from the description below.

The seal portion 48 and collet portion 52 define first and second interior axial bore portions 60 and 62, respectively. The first and second interior axial bore portions 60 and 62 are substantially identical in diameter and cross-sectional shape such that when aligned, the first and second interior axial bore portions 60 and 62 define a substantially smooth interior cylindrical passageway 64 of constant diameter. The interior cylindrical passageway 64 is configured to slidably receive a portion of a UHPLC fluid conduit therein. Preferably, the interior cylindrical passageway 64 receives stainless steel tubing 34 of a predetermined outer diameter having an internal fluid passageway 42. It should be appreciated that the first and second interior axial bore portions 60 and 62 may be any suitable size to define an interior cylindrical passageway 64 of a suitable diameter for receiving tubing of a desired size, material, etc., for different applications.

Both the seal portion 48 and the collet portion 52 are of a generally frusto-conical or cone shape to define a double-ended hybrid ferrule 40 when mated together. The seal portion 48 includes a tapered end 54 and an enlarged end 58, wherein the enlarged end 58 defines a transverse end surface 66. An exterior, substantially smooth tapered surface 56 extends from the enlarged end 58 to the tapered end 54 such that the seal portion 48 is suitably sized and shaped to be received within a portion of a threaded fitting. More specifically, the seal portion 48 is configured to be tightly received within the female, cone-shaped chamber 28 of the well known threaded fitting 18 described above with respect to FIG. 1 (the same threaded fitting 18 is shown in FIGS. 5A and 5B and will be described in further detail below).

Moreover, with the seal portion 48 being made from a suitable material such as PEEK, the seal portion seals against the fitting 18 and around the stainless steel tubing 34 to form a liquid-tight seal without deforming the stainless steel tubing 20. In this manner, the seal portion 48 forms a soft swage on the tubing 20 so that the hybrid ferrule 40 can be repositioned on the tubing 34 and reused in other fittings.

Figure 1:
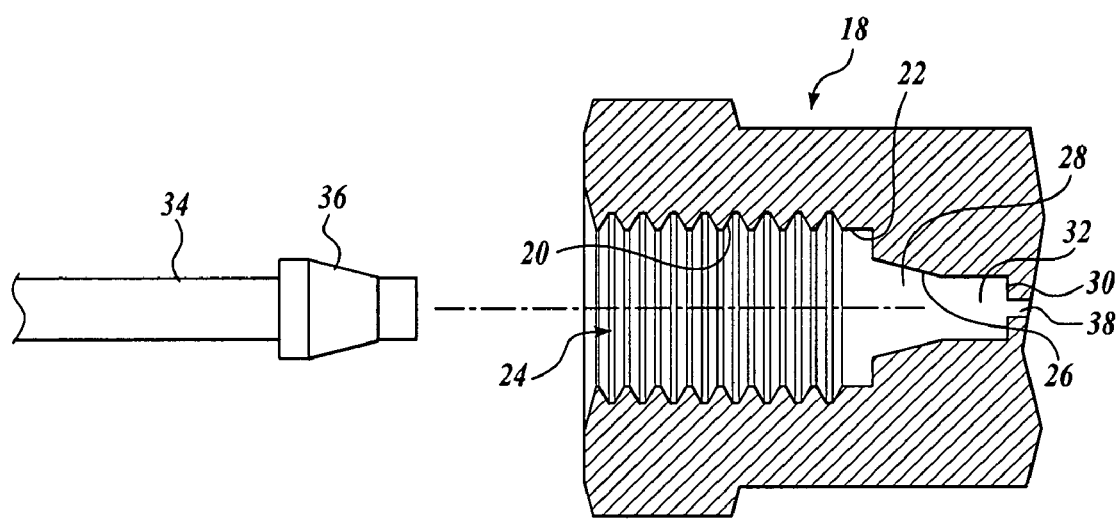
FIG. 1 is a partial cross-sectional view of a prior art fitting assembly for use in fluid transfer assemblies.
Figure 5A:
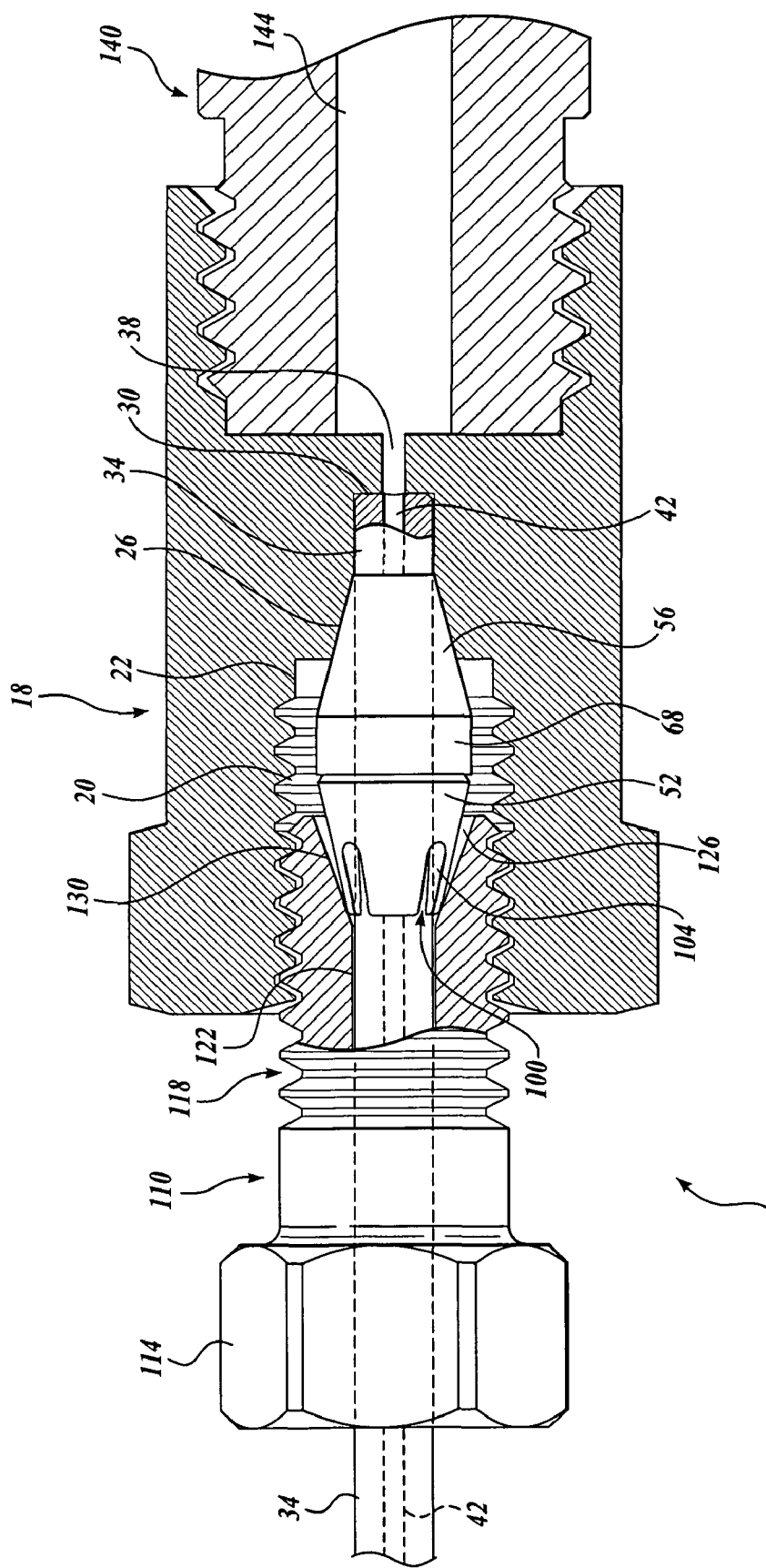
FIG. 5A is a partial cross-sectional view of a fitting assembly for use in fluid transfer assemblies, wherein the hybrid ferrule of FIG. 2 is received within the fitting assembly.
Figure 5B:
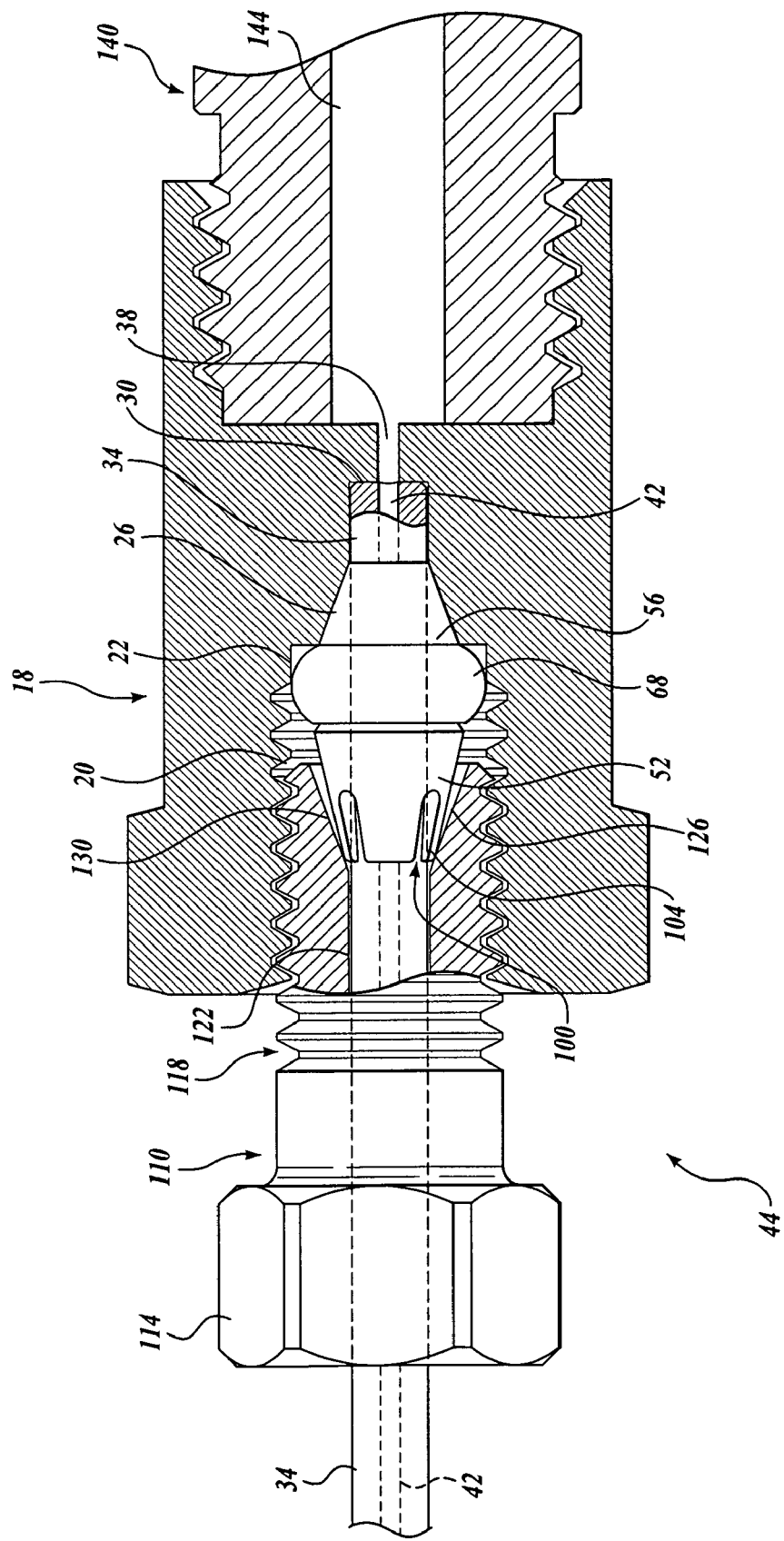
FIG. 5B is a partial cross-sectional view of a fitting assembly for use in fluid transfer assemblies, wherein the hybrid ferrule of FIG. 2 is received within the fitting assembly.

Preferably, the seal portion 48 defines a forty degree cone such that it is suitably adapted to be received within a variety of well-known threaded fittings similar to the fitting shown in FIGS. 1, 5A, and 5B. Such threaded fittings are readily available from a variety of well known manufacturers, such as Optimize Technologies, Inc., Swagelok Company, Parker Hannifin Corp, Valco Instruments Company Inc., Rheodyne and Upchurch Scientific (both part of the IDEX Health & Science Group), etc. For instance, the seal portion 48 may receive a 1/16th inch outer diameter tubing and fit within a standard 1/16th inch swaged fitting. It should be appreciated that the seal portion 48 may instead be larger or smaller in size to fit within various fittings for different applications.

The seal portion 48 further includes an annular collet-engaging protrusion 68 that extends axially from the end surface 66 of the seal portion 48. The annular collet-engaging protrusion 68 defines a substantially cylindrical outer surface 72 that extends from the tapered surface 56 of the of the seal portion 48. The cylindrical outer surface 72 includes a center longitudinal axis that is substantially collinear with the cylindrical passageway 64 of the hybrid ferrule 40. It should be appreciated that the outer surface 72 of the annular collet-engaging protrusion 68 may instead be curved or any other suitable contour. The annular collet-engaging protrusion 68 includes an inwardly extending lip 74 on its distal end that defines an annular receptacle or groove 76 between the lip 74 and the enlarged end surface 66 of the seal portion 48. The groove 76 is sized and configured to receive a lip 78 of a correspondingly shaped protrusion 82 of the collet portion 52.

The protrusion 82 of the collet portion 52 extends axially outwardly from a transverse end surface 92 of the collet portion 52 such that its center longitudinal axis is substantially collinear with the cylindrical passageway 64 of the hybrid ferrule 40. Moreover, the inner surface of the protrusion 82 extends from and is in substantial alignment with the surface of the second interior axial bore portion 62. In this manner, the interior surface of the cylindrical passageway 64 remains substantially smooth and of constant diameter such that the hybrid ferrule 40 may slidably receive a portion of UHPLC tubing or other suitable tubing therein. The lip 78 extends outwardly from the protrusion 82 to define an annular receptacle or groove 84 between the lip 78 and the end surface 92 of the collet portion 52. The groove 84 is sized and shaped to receive the lip 78 of the protrusion 68 extending from the seal portion 48.

As shown in FIG. 4, the collet portion 52 is secured to the seal portion 48 by mating the protrusion 82 of the collet portion 52 with the protrusion 68 of the seal portion 48. More specifically, the lip 78 of protrusion 82 is received within annular groove 76, and the lip 74 of protrusion 68 is received within annular groove 84. In this manner, the collet portion 52 and seal portion 48 are "snap fit" together to define the hybrid ferrule 40. With the collet portion 52 being made from Titanium and the seal portion 48 being made from PEEK, the collet portion 52 and seal portion 48 are preferably permanently secured together once assembled. In any event, it is preferred that the seal portion 48 be sufficiently secured to the collet portion 52 such that the hybrid ferrule 40 remains intact (the seal portion 48 remains connected to the collet portion 52) when removing the hybrid ferrule 40 from the fitting 18. Moreover, it should be appreciated that the seal portion 48 may instead be molded or otherwise formed on the collet portion 52 in any manner well known in the art.

As stated above, the collet portion 52 is of a generally frusto-conical or cone shape. Similar to the seal portion 48, the collet portion 52 includes a tapered end 86 and an enlarged end 88, wherein the enlarged end 88 defines a transverse end surface 92. An exterior, substantially smooth tapered surface 96 extends from the enlarged end 88 to the tapered end 86 such that the collet portion 52 is suitably sized and shaped to be received within a portion of a second fitting, or threaded nut 110. More specifically, and as shown in FIGS. 5A and 5B, the collet portion 52 is configured to be tightly received, or wedged within the female, cone-shaped chamber 126 of a well known externally torqued hexagonal nut 110. The nut 110 is threadably engageable with the threaded fitting 18 to compress and secure the collet potion 52 onto the tubing 34. Preferably, the collet portion 52 is configured to be received within the female, cone-shaped chamber 126 of an OPTI-LOK EXP 10-32 Hex Head Male Nut, available from Optimize Technologies, Inc., of Oregon City, Oreg. However, it should be appreciated that any other suitable nut, fitting, tightening device, or clamping device may be used to suitably compress the collet portion 52 onto the tubing 34.

The collet portion 52 further includes a plurality of axial slots 100 extending from the tapered end 86 along at least a portion of the collet portion 52 to define a plurality of axially extending fingers 104. Preferably, the collet portion 52 includes four axial slots 100 spaced equidistant from one another circumferentially about the tapered end 86 of the collet portion 52 to define four substantially identical axially extending fingers 104. However, it should be appreciated that any suitable number of axially extending fingers 104 may be used. In any event, it is preferred that a suitable number of fingers be defined and the fingers be of a suitable width and length such that they may be deformed onto the tubing 34 when engaged by the nut 110 without breaking off from the collet portion 52.

The fingers 104 deform or contract radially onto the tubing 34 when an external axial force is exerted on the fingers 104 by the female, cone-shaped chamber 126 of the nut 110. In this manner, the collet portion 52 is secured onto the tubing 34 to prevent the tubing 34 from ejecting at extreme pressures. With the collet portion 52 being made from a Titanium alloy or another suitable material, the fingers 104 spring back into their original position when the nut 110 is disengaged from the collet portion 52 such that the tubing 34 may be readjusted or removed from the ferrule 40. In addition, the collet portion 52 does not form a hard swage on the stainless steel tubing 34.

Moreover, as stated above, the seal portion 48 is made from PEEK or another suitable material such that it may seal within the fitting 18 without forming a hard swage on the tubing 34. Thus, the hardened Titanium collet portion 52 married to the softer PEEK seal portion 48 provides a hybrid ferrule 40 that seals in the female, cone-shaped chamber 28 of the fitting 18 while providing the grip necessary to prevent the stainless steel tube 34 from ejecting at high pressures. Moreover, the hybrid Titanium PEEK ferrule 40 secures onto the tubing without swaging irreversibly onto the tubing 34.

Thus, the hybrid ferrule 40 provides the necessary grip to withstand extreme pressures while providing the adjustability to be used in fittings of different sizes and tolerances. The adjustability feature is desirable, for example, when using either different female 1/16th inch pieces from the same manufacturer or when using 1/16 inch female fittings from different manufacturers. In the first case, there are slight differences with respect to the tube stop depth because of manufacturing tolerances, and the hybrid ferrule 40 needs to be repositioned on the tubing 34 to enable the tubing to bottom out in the cylindrical chamber 32 of the fitting 18. In the second instance, with different manufacturer's dimensions, the tube stop depth may differ by as much as 0.040 inches. Without the use of the hybrid ferrule 40, the tubing would either bottom out before the ferrule could engage the frusto-conical sealing surface 26 of the cone-shaped chamber 28 to make a seal, or the tubing would be off the bottom of the cylindrical chamber 32 measurably. Thus, the adjustability of the hybrid ferrule 40 enables the ferrule 40 to be reused in various fittings.

Referring to FIGS. 5A and 5B, a description of the hybrid ferrule 40 in use with a portion of the UHPLC fitting assembly 44 will be hereinafter described. The UHPLC fitting assembly 44 includes a fitting 18 as described above with respect to FIG. 1. More specifically, the threaded fitting 18 includes an internally threaded portion 20 formed near a first open end that is suitable for threadably receiving the external threads of the nut 110. The fitting 18 further includes a female, cone-shaped chamber formed at its distal, internal end that defines a frusto-conical sealing surface 26. The cone-shaped chamber is in communication with a cylindrical chamber sized to receive the end of the tubing 34 therein.

The fitting 18 further includes a passage 38 that is in communication with the cylindrical chamber and aligns with the fluid passageway 42 of the tubing 34 when the tubing is received within the cylindrical chamber. The fitting 18 may be threadably connected to a connection device 140 at a second open end of the fitting for placing the tubing 34 into communication with, for instance, a column, trap, etc., received within a cylindrical opening 144 in the connection device 140. It should be appreciated that the connection device 140 may be any suitable device used in UHPLC systems or other suitable systems.

To assemble the fitting assembly 44, the tubing 34 is inserted within the cylindrical bores of the nut 110 and the hybrid ferrule 40, and the tubing 34 is thereafter inserted into the fitting 18. The tubing 34 is moved into the fitting 18 until the tubing 34 is received within the cylindrical chamber of the female port such that the tubing is substantially bottomed out against the tube stop 30. Thereafter, the nut 110 may be tightened within the fitting to secure the hybrid ferrule 40 in its position on the tubing 34 and to define a liquid-tight seal between the tubing 34 and the fitting 18.

As described briefly above, the nut 110 is a well known externally torqued hexagonal nut that is threadably engageable with the threaded fitting 18 to compress and secure the collet potion 52 of the hybrid ferrule 40 onto the tubing 34. The nut 110 includes an enlarged end 114 that may be hex-shaped or any other suitable contour such that the nut 110 may be easily tightened within the fitting either by hand or with a suitable tool. The nut includes a threaded portion 118 extending from the enlarged end 114 and a cylindrical bore 122 extending axially along the center of the nut 110. The cylindrical bore 122 widens at the threaded end of the nut to define a frusto-conical chamber 126 having a collet-engaging surface 130.

The frusto-conical chamber 126 is sized and shaped to engage the collet portion 52 of the hybrid ferrule 40 and exert an axial force on the collet portion 52 as the nut 110 is tightened into the fitting 18. As shown in FIG. 5A, the collet-engaging surface 130 engages the fingers 104 of the collet portion 52 to compress the fingers 104 onto the tubing 34 as the nut 110 is tightened. At the same time, the collet portion 52 imparts an axial force against the seal portion 56 to drive the seal portion into sealing engagement with the frusto-conical sealing surface 26 of the fitting 18. More specifically, referring back to FIG. 4, the protrusion 82 of the collet portion 52 engages and imparts an axial force on the end surface 66 of the seal portion 48 to drive the seal portion 48 into sealing engagement against the frusto-conical sealing surface 26 of the fitting 18. As such, the seal portion 48 is sealingly engaged with the fitting 18 while the collet portion 52 is secured on the tubing 34.

When it is desired to remove the tubing 34 from the fitting 18, the nut 110 is loosened until the collet-engaging surface 130 of the nut 110 no longer substantially engages the fingers 104 of the collet portion 52. When this occurs, the fingers 104 spring back into their original state such that the tubing 34 may slide out from within the hybrid ferrule 40. Moreover, when the nut 110 and tubing 34 are removed from the fitting 18, the hybrid ferrule 40 may be removed from the fitting 18 for use in a different application or fitting. If the seal portion 56 is "stuck" within the cone-shaped portion of the fitting 18, the seal portion 48 may be pulled out of sealing engagement with the fitting 18 by pulling on the collet portion 52.

Referring to FIG. 5B, when the nut 110 is over-tightened within the fitting 18, the protrusion 82 of the collet portion 52 imparts an axial force on the end surface 66 of the seal portion 48 to further compress the seal portion 48. Because the seal portion 48 is made from PEEK or another suitable material, the over tightening causes a section of the seal portion 48 external of the cone-shaped portion of the fitting 18 to bulge outwardly into the space defined by the threaded and non-threaded portions 20 and 22 of the fitting 18. Such over tightening does not adversely affect the sealing properties of the sealing portion 48. Moreover, when it is desired to remove the tubing 34 from the fitting, the hybrid ferrule 40 can be removed from the fitting in one piece and can be re-used in its deformed state in another fitting. Thus, even when the nut 110 is fully tightened within the fitting 18, the hybrid ferrule properly seals within the fitting and secures on the tubing 34 to function in UHPLC systems.

Thus, it can be seen from the foregoing that the hybrid ferrule 40 constructed of a PEEK seal portion 48 secured to a Titanium collet portion 52 provides a ferrule that remains secured on tubing when used in extreme pressure systems while maintaining a liquid-tight seal within the fittings, wherein the ferrule may be re-used or adjusted within the fitting to accommodate various applications, fitting sizes, etc. While the preferred embodiment of the invention has been illustrated and described, it will be appreciated that various changes can be made therein without departing from the spirit and scope of the present disclosure.

The embodiments of the present disclosure in which an exclusive property or privilege is claimed are defined as follows:

1. A ferrule for use in a fluid transfer assembly having a fluid conduit, the ferrule comprising:
   (a) a frusto-conical seal portion having a tapered end and an enlarged end, the frusto-conical seal portion have a first cylindrical bore sized and configured to slidably receive a fluid conduit made from a predetermined material having a hardness, the seal portion formed from a first material suitable to seal the fluid conduit within a first fitting without substantially deforming the fluid conduit, the first material having a hardness no greater than the hardness of the fluid conduit; and
   (b) a frusto-conical collet portion having a tapered end and an enlarged end, the enlarged end of the collet portion mated with the enlarged end of the seal portion, the collet portion having a second cylindrical bore in substantial alignment with the first cylindrical bore, the collet portion including at least one axial finger extending along the tapered end that is configured to be biased into locking engagement with the fluid conduit, wherein the collet portion is formed from a second material that substantially prevents deformation of the fluid conduit when the finger is biased into locking engagement with the fluid conduit, the second material having a hardness no less than the hardness of the fluid conduit.

2. The ferrule of claim 1, wherein the seal portion is formed from Polyetheretherketone.

3. The ferrule of claim 1, wherein the collet portion is formed from a Titanium alloy.

4. The ferrule of claim 1, wherein the collet portion includes four axially extending fingers spaced substantially equidistant circumferentially about the tapered end of the collet portion.

5. The ferrule of claim 1, wherein the seal portion includes a first axial protrusion having a lip that is mateable with a second correspondingly shaped protrusion extending axially from the collet portion.

6. The ferrule of claim 1, wherein the seal portion is molded onto the collet portion.

7. A ferrule for use in a fluid transfer assembly having a fluid conduit and a first fitting mateable with a second fitting, the ferrule removably receivable on the fluid conduit and configured to removably secure the fluid conduit between the first and second fittings, the ferrule comprising:
   (a) a frusto-conical seal portion have a first cylindrical bore sized and configured to slidably receive the fluid conduit made from a predetermined material having a hardness, the seal portion formed from a first material suitable to seal the fluid conduit within the first fitting without substantially deforming the fluid conduit, the first material having a hardness no greater than the hardness of the fluid conduit; and
   (b) a frusto-conical collet portion mated with the seal portion and having a second cylindrical bore in substantial alignment with the first cylindrical bore, the collet portion including at least one axial finger that is biased into locking engagement against the fluid conduit when the first fitting is mated with the second fitting, wherein the collet portion is formed from a second material that allows the collet portion to lockingly engage the fluid conduit without substantially deforming the fluid conduit, the second material having a hardness no less than the hardness of the fluid conduit.

8. The ferrule of claim 7, wherein the seal portion is formed from Polyetheretherketone.

9. The ferrule of claim 7, wherein the collet portion is formed from a Titanium alloy.

10. The ferrule of claim 7, wherein the collet portion includes a tapered end and an enlarged end.

11. The ferrule of claim 10, wherein the collet portion includes four axially extending fingers spaced substantially equidistant circumferentially about the tapered end of the collet portion.

12. The ferrule of claim 7, wherein the seal portion is securely mated with the collet portion such that the seal portion remains attached to the collet portion when the ferrule is removed from within the first fitting.

13. A fitting assembly for a fluid transfer assembly, the fitting assembly comprising:
   (a) a fluid conduit;
   (b) a first fitting having an opening for slidably receiving the fluid conduit made from a predetermined material having a hardness;
   (c) a second fitting having an opening for slidably receiving the fluid conduit, wherein the second fitting is lockingly engageable with the first fitting;
   (d) a ferrule removably receivable on the fluid conduit and configured to removably secure the fluid conduit between the first and second fittings, the ferrule comprising:
      (i) a frusto-conical seal portion slidably received on the fluid conduit, the seal portion formed from a first material suitable to seal the fluid conduit within the first fitting without substantially deforming the fluid conduit, the first material having a hardness no greater than the hardness of the fluid conduit; and
      (ii) a frusto-conical collet portion mated with the seal portion and slidably received on the fluid conduit, the collet portion including at least one axial finger that is biased into locking engagement against the fluid conduit when the first fitting is mated with the second fitting, wherein the collet portion is formed from a second material that allows the collet portion to lockingly engage the fluid conduit without substantially deforming the fluid conduit, the second material having a hardness no less than the hardness of the fluid conduit.

14. The fitting assembly of claim 13, wherein the first fitting defines a cylindrical chamber for receiving the fluid conduit, the cylindrical chamber having an interior end surface against which an end of the fluid conduit may abut.

15. The fitting assembly of claim 14, wherein the seal portion is configured to sealing engage the fluid conduit within the first fitting such that the end of the fluid conduit abuts the interior end surface of the cylindrical chamber of the first fitting.

16. The fitting assembly of claim 15, wherein the ferrule and fluid conduit are removable from the first fitting such that the ferrule may be repositioned on the fluid conduit and reused within a third fitting having a cylindrical chamber for receiving the fluid conduit, the cylindrical chamber having an interior end surface against which the end of the fluid conduit may abut.

17. The fitting assembly of claim 16, wherein the seal portion is configured to sealingly engage the fluid conduit within the third fitting such that the end of the fluid conduit abuts the interior end surface of the cylindrical chamber of the third fitting.

18. The fitting assembly of claim 13, wherein the second fitting includes a frusto-conical chamber that exerts an axial force on the collet portion when the second fitting is engaged with the first fitting.

19. The fitting assembly of claim 18, wherein the collet portion exerts an axial force on the seal portion to seal the fluid conduit within the first fitting when the second fitting is engaged with the first fitting.

20. The fitting assembly of claim 13, wherein the second fitting includes a frusto-conical chamber that engages the collet portion to compress the at least one axial finger into locking engagement against the fluid conduit when the second fitting is engaged with the first fitting.

21. A ferrule for use in a fluid transfer assembly having a fluid conduit, the ferrule comprising:
   (a) a frusto-conical seal portion having a tapered end and an enlarged end, the frusto-conical seal portion have a first cylindrical bore sized and configured to slidably receive a fluid conduit made from a predetermined material having a hardness, the seal portion formed from a first material suitable to seal the fluid conduit within a first fitting without substantially deforming the fluid conduit, the first material having a hardness no greater than the hardness of the fluid conduit; and
   (b) a collet portion having a second cylindrical bore in substantial alignment with the first cylindrical bore, the collet portion including at least one axial finger extending along the tapered end that is configured to be biased into locking engagement with the fluid conduit, wherein the collet portion is formed from a second material that substantially prevents deformation of the fluid conduit when the finger is biased into locking engagement with the fluid conduit, the second material having a hardness no less than the hardness of the fluid conduit.

* * * * *

UNITED STATES PATENT AND TRADEMARK OFFICE
CERTIFICATE OF CORRECTION

PATENT NO. : 8,201,854 B2 Page 1 of 1
APPLICATION NO. : 12/476931
DATED : June 19, 2012
INVENTOR(S) : Ford et al.

It is certified that error appears in the above-identified patent and that said Letters Patent is hereby corrected as shown below:

COLUMN      LINE

Title Page
Item [75]                        "Cobett, OR" should read --Corbett, OR--

In the Claims

Col. 9          Line 49        "sealing engage" should read
Claim 15                       --sealingly engage--

Signed and Sealed this
Nineteenth Day of November, 2013

Teresa Stanek Rea
*Deputy Director of the United States Patent and Trademark Office*